US010877295B2

(12) United States Patent
Otts et al.

(10) Patent No.: US 10,877,295 B2
(45) Date of Patent: Dec. 29, 2020

(54) MULTI-COMPONENT CONTACT LENS HAVING POSTERIOR AND ANTERIOR FEATURES

(71) Applicant: Verily Life Sciences LLC, South San Francisco, CA (US)

(72) Inventors: Daniel B. Otts, Pleasanton, CA (US); Jeremy L. Emken, San Jose, CA (US); Joshua N. Haddock, Mountain View, CA (US); James D. Riall, Saint Johns, FL (US); James W. Haywood, Fleming Island, FL (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 16/544,404

(22) Filed: Aug. 19, 2019

(65) Prior Publication Data
US 2019/0369414 A1    Dec. 5, 2019

Related U.S. Application Data

(63) Continuation of application No. 15/274,255, filed on Sep. 23, 2016, now Pat. No. 10,423,010.

(51) Int. Cl.
*G02C 7/04* (2006.01)
*A61F 2/16* (2006.01)

(52) U.S. Cl.
CPC .............. *G02C 7/04* (2013.01); *A61F 2/16* (2013.01); *A61F 2/1601* (2015.04); *G02C 7/047* (2013.01); *G02C 7/048* (2013.01)

(58) Field of Classification Search
CPC ..... G02C 7/00; G02C 7/02; G02C 7/04; G02C 7/048; G02C 7/049
See application file for complete search history.

(56) References Cited

U.S. PATENT DOCUMENTS

| 3,246,941 A | 4/1966 | Moss |
| 4,621,912 A | 11/1986 | Meyer |
| 5,347,326 A | 9/1994 | Volk |

(Continued)

FOREIGN PATENT DOCUMENTS

| EP | 2 778 750 A1 | 9/2014 |
| JP | 2007195818 A | 8/2007 |

(Continued)

OTHER PUBLICATIONS

PCT/US2017/052810, International Search Report and Written Opinion of the International Searching Authority, dated Nov. 28, 2017, 14 pages.

(Continued)

*Primary Examiner* — Robert E. Tallman
(74) *Attorney, Agent, or Firm* — Christensen O'Connor Johnson Kindness PLLC

(57) ABSTRACT

An ophthalmic device having posterior and anterior features are disclosed herein. An example ophthalmic device may include an enclosure having an insert disposed therein. The enclosure may include a cornea contact disposed on a posterior side and arranged to rest on a user's cornea outside of a central cornea area when the ophthalmic device is worn by a user. The enclosure further includes a channel formed in the posterior side, where the channel extends through the cornea contact from at least radially outside of the insert to an inner edge of the cornea contact.

20 Claims, 5 Drawing Sheets

(56) References Cited

U.S. PATENT DOCUMENTS

| | | |
|---|---|---|
| 6,726,322 B2 | 4/2004 | Andino et al. |
| 6,779,888 B2 | 8/2004 | Marmo |
| 8,673,340 B2 | 3/2014 | Rosenthal |
| 2012/0234493 A1 | 9/2012 | Pugh et al. |
| 2014/0268019 A1 | 9/2014 | Riall |
| 2015/0138500 A1 | 5/2015 | de Juan, Jr. et al. |
| 2015/0290034 A1 | 10/2015 | Blum et al. |
| 2016/0079631 A1 | 3/2016 | Flitsch et al. |

FOREIGN PATENT DOCUMENTS

| | | |
|---|---|---|
| WO | 90/08339 A1 | 7/1990 |
| WO | 02/27388 A1 | 4/2002 |

OTHER PUBLICATIONS

Chinese Office Action, with English Translation, for Chinese Patent Application No. 201780065606.5, dated Jan. 14, 2020, 24 pages.
Chinese Office Action for Chinese Patent Application No. 201780065606.5, dated Jul. 8, 2020, 7 pages.

MULTI-COMPONENT CONTACT LENS HAVING POSTERIOR AND ANTERIOR FEATURES

CROSS-REFERENCE TO RELATED APPLICATION

This application is a continuation of U.S. application Ser. No. 15/274,255, filed on Sep. 23, 2016, the contents of which are incorporated herein by reference.

TECHNICAL FIELD

This disclosure relates generally to an ophthalmic device, and in particular, relates to a wearable contact lens.

BACKGROUND INFORMATION

On-eye wearable ophthalmic devices, such as contact lenses, may be formed in a variety of structures, such as soft contact lenses, hard contact lenses, and hybrid contact lenses, to name a few. A hybrid contact lens is a combination of soft and hard contact lens technologies. The various structures have their own advantages and disadvantages. For example, soft lenses may be easier to fit and be more comfortable to wear than hard lenses, but they may not provide quality optics as do the hard lenses. Conversely, hard lenses may be difficult to fit, which typically require iterative fittings with different curvatures to settle on a comfortable fit. While hybrid lenses may provide some combination of the benefits of each, they may typically still require multiple fittings to obtain the desired comfortable fit.

While various designs have been tried, the disadvantages of the various designs persist. These disadvantages, if not addressed, may increase the complexity of design, manufacturing and stock maintenance of future lenses. As such, it may be desirable to reduce or eliminate such disadvantages.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
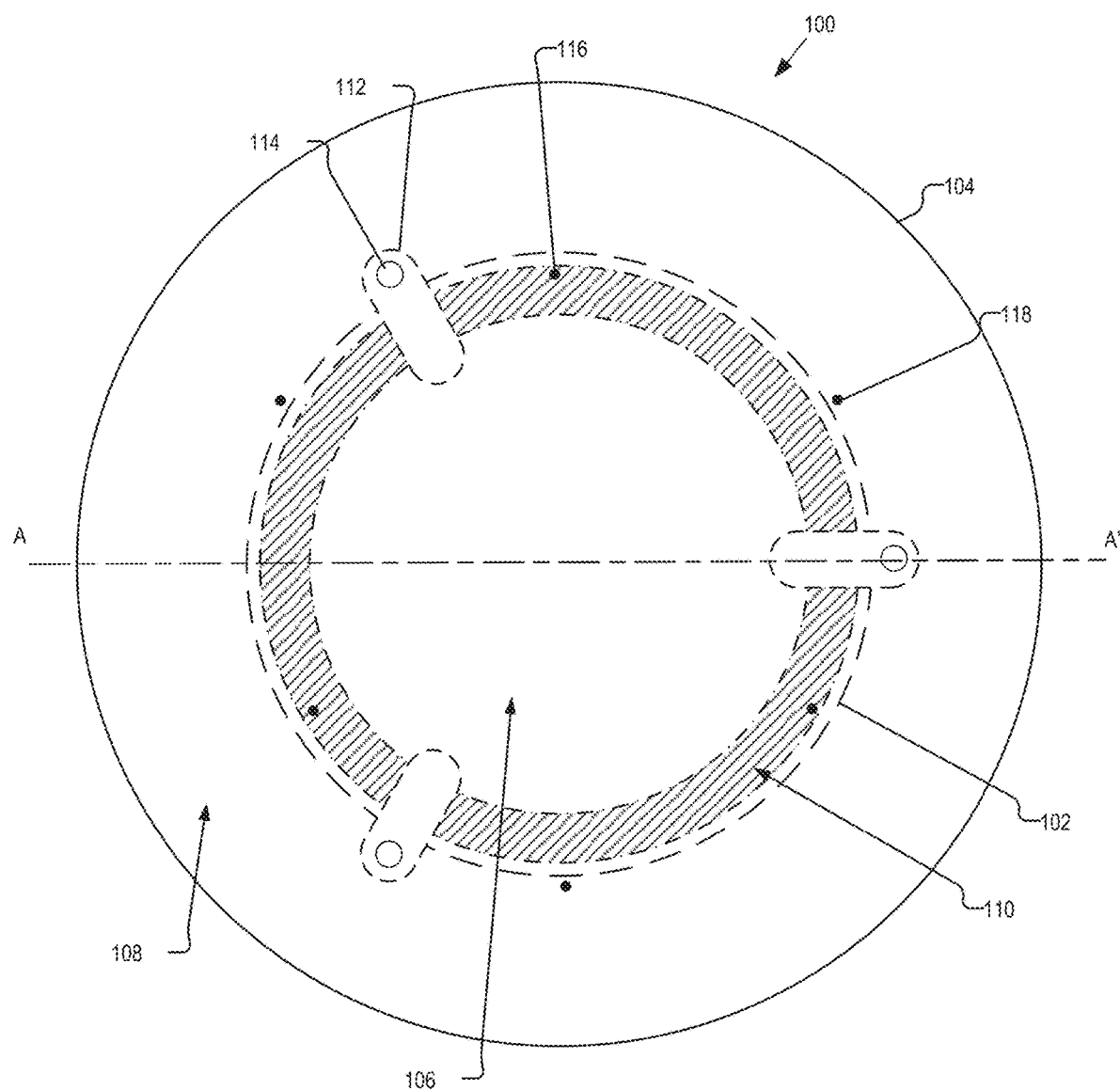
FIG. 1 is an illustrative plan view of an ophthalmic system including posterior and anterior features in accordance with an embodiment of the disclosure.

Embodiments of an ophthalmic device having tear fluid exchange features, and alignment features are described herein. For example, channels formed on a posterior side of the ophthalmic device may provide for tear fluid exchange between the cornea under the ophthalmic device and the eye external to the ophthalmic device. Additionally, features formed on an anterior side of the ophthalmic device may provide for alignment of an insert of the ophthalmic device with an enclosure of the ophthalmic device. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As discussed above, the various conventional contact lens structures all have their own advantages and disadvantages. These advantages and disadvantages may also affect smart contact lenses. The advent of electronic lenses, e.g., smart contact lenses, may include electronics and sensors that provide various functionality. Such electronic lenses, however, may be similar in structure to hybrid lenses due to the electronics and sensors being desirably enclosed in a biocompatible material. Smart contact lenses may include dynamic optics and associated control electronics, which may provide accommodation through the control of the dynamic optic. Smart contact lenses may be similar in structure to hybrid lenses in that they include an insert disposed within an enclosure, where the insert may house the dynamic optics and associated control. Hybrid lens-type structures, however, may include various problems that may affect their wearability and fitting. These features may pose difficulties in fabrication and adoption of smart contact lenses by the lens-wearing public.

For example, hybrid lenses may require iterative fittings to ensure proper fit on a user's eye. The difficulty in fitting may be due to the insert, which may be rigid, and how the insert affects the comfort of the lens. Additionally, suction of the hybrid lens to the user's eye may cause difficulty in removal by the user, which may cause incidents of requiring their removal by an eye care provider. Exchange of tear fluid from on and around the central cornea with fresh tear fluid may also be difficult if the hybrid lens does not include passageways for such exchange. In some instances, lack of fresh tear fluid and oxygen may lead to damage of the cornea. The problem with suction and the lack of tear fluid exchange may be due to the same hybrid lens features, and may both be present.

Moreover, due to the iterative fitting process, each pair of hybrid lenses are essentially personalized, which requires fabrication of numerous hybrid lenses. The number of hybrid lenses, which may equal the number of wearers, may complicate manufacturing, assembly, and inventory management.

As such, it may be desirable to have a small number of hybrid lens designs per optical prescription. Such hybrid lenses may ease manufacturing allowing for high volume processing instead of individualized fabrication. Additionally, the one or two hybrid lenses may include features that allow for the exchange of tear fluid and ease of lens removal, e.g., that also reduce or eliminate the incident of suction. Further, the hybrid lens may include alignment features that may simplify assembly and that provide alignment fiducials for obtaining centricity between an insert and an enclosure.

For example, the present disclosure may provide for an enclosure that may encapsulate a pre-formed semi-rigid to rigid insert such as a rigid gas permeable contact lens or an electronic insert, rigid or soft. The enclosure may include geometries and/or features that may provide a variety of benefits. For example, the enclosure's features may provide a means for aiding fabrication during over molding of contact lens enclosure material by incorporating internal standoff features. Additionally, enclosure features may provide anterior channel/vent contours that may prevent or reduce the incidence of mechanical suction of the lens to the eye during wear, thereby facilitating lens removal. The enclosure may include posterior contours that allow the contact lens to fit onto a wide population of contact lens wearers. The enclosure features may further provide fiducials useful as assembly aids and/or post-fabrication inspection. Lastly, the enclosure may include geometries and features that may provide enhanced tear fluid exchange in and around the central cornea region.

FIG. 1 is an illustrative plan view of an ophthalmic device 100 including posterior and anterior features in accordance with an embodiment of the present disclosure. The ophthalmic device 100 may be an on-eye wearable device or an implantable device. The ophthalmic device 100, for example, may be placed over a user's cornea to provide various optical and/or benefits, such as vision correction, accommodation, medical monitoring, and the like. Alternatively, the ophthalmic device 100 may be an intraocular device amenable to implantation into a user's eye. The ophthalmic device 100 may include an insert 102 disposed in an enclosure 104. The enclosure 104 may have various features formed on a posterior and/or an anterior side to enhance wearability and/or assembly. In some embodiments, the posterior side and/or anterior side features may have discrete rotational symmetry of the nth order, where n may be an odd number greater than or equal to three.

The insert 102 may provide optical properties to the ophthalmic device 100, such as static and/or dynamic optical power, and may be positioned over a central area of a user's cornea when the ophthalmic device is worn on the eye. The insert 100 may have the form of a semi-spherical shell having a diameter, a radius of curvature of a posterior side and a radius of curvature of an anterior side. The posterior side may be an eye-facing side, whereas the anterior side may be an external facing side. Stated another way, the posterior side may be concave and the anterior side may be convex. In some embodiments, the insert 102 may be around 10 mm in diameter, and have a radius of curvature on the posterior side of around 8 mm. The insert 102 may have various thicknesses, and in some embodiments may change in thickness in a radial direction from a central axis to a perimeter. The thickness of the insert, however, may be a non-limiting aspect of the present disclosure.

The insert 102 may be rigid or soft. In some embodiments, the insert 102 may be a pre-formed rigid insert that is formed from a rigid, gas permeable polymer. In some embodiments, the insert 102 may be soft, and formed from a biocompatible elastomer, such as a silicone elastomer, for example. In some embodiments, the insert 102 may include control logic and a dynamic optic controlled by the control logic. Additionally, in some embodiments, the insert 102 may be formed from multiple components. In general, the insert 102 may be enclosed in the enclosure 104 and, when worn by a user, be centrally located over the user's cornea to provide one or more optical properties to the user.

The enclosure 104 may envelope the insert 102 and may include various features, such as contours, ridges, fenestrations, bumps, etc., that provide various assembly and wearability aspects to the ophthalmic device 100. The enclosure 104 may be formed from a flexible, biocompatible polymer. For example, the enclosure 104 may be formed from a hydrogel, silicone hydrogel, or silicone elastomer. The enclosure 104 may also be referred to as an over mold or an encasement. Similar to the insert 102, the enclosure 104 may have the form of a semi-spherical shell having a diameter, a posterior side, e.g., eye-ward facing side, and an anterior side, e.g., external facing side. The posterior side may be concave and correspond to the posterior side of the insert 102, while the anterior side may be convex and correspond to the anterior side of the insert 102. The posterior side may be characterized by having multiple radii of curvatures, which may be different in different areas of the ophthalmic device 100. For example, a radius of curvature of the enclosure 104 in a center area 106, which may include the diameter of the insert 102, may be different than a radius of curvature of the enclosure 104 in a skirt area 108, which may be radially outside of the insert 102. The center area 106 may also be referred to herein as the optical area 106. Desired radii of curvature for the center area 106 and the skirt 108 may allow the ophthalmic device 100 to fit a majority of the eye population. The anterior side may have different radii of curvature, or it may have a single radii of curvature. The radii of curvature of the anterior side may be such as to correct for one or more of myopia, hyperopia, presbyopia, and/or astigmatism of the wearer, for example. Further, the diameter of the enclosure 104 may be greater than the diameter of the insert 102. For example, the diameter of the enclosure 104 may range from 13 to 16 mm.

The enclosure 104 may include a cornea contact 110 formed therein and disposed at least under a portion of the perimeter of the insert 102 on the posterior side of the enclosure 104. The cornea contact 110 may be a discontinuous toroidal-shaped ring that provides a cornea contact area to the ophthalmic device 100. The cornea contact 110 may contact the user's eye outside of the central cornea to position the ophthalmic device 100 over an optic area of the eye. An amount of area of the cornea contact 110 may affect the wearability, e.g., comfort, of the ophthalmic device 100, with more area improving comfort. While increasing the area of the cornea contact 110 may improve wearability, the amount of area available may be limited, at least in part, by the center area 106.

The cornea contact 110 may be formed from a raised area on the posterior side of the ophthalmic device 100. For example, the cornea contact 100 may be formed in or on a posterior side of the enclosure 104. Depending on the height of the cornea contract 110, an amount of clearance between a posterior side of the enclosure 104 and the central cornea of the user's eye may be obtained. The clearance may form a chamber between the central cornea and the posterior side of the ophthalmic device 100 which may be, at least partially, encircled by, e.g., enclosed by or at least partially enclosed by, the cornea contact 110. The chamber, which may also be referred to herein as a tear fluid chamber, may provide a volume for tear fluid to accumulate over the central cornea.

The enclosure 104 may further include one or more channels 112. The channels 112 may be formed in or on the posterior side of the enclosure 104 and may extend through the cornea contact 110 in one or more areas. In some embodiments, the channels 112 may form the discontinuous portions of the cornea contact 110. Each of the channels 112 may extend from at least a radius outside of the insert 102 to an internal edge of the cornea contact 110, which may be close to the center area 106. In some embodiments, the channels 112 may extend to at least an outside edge of the central cornea of the user's eye. In some embodiments, one or more of the channels 112 may extend radially outward and terminate at an edge of the enclosure 104. While there are three channels 112 shown in FIG. 1, the number of channels and their symmetry is a non-limiting aspect. In general, it may be desirable to include an odd number of channels 112 so to ensure an open channel in case of symmetric physical characteristics of the eye close off channels that may align with such physical characteristics. For example, including an odd number of channels 112 may prevent the ophthalmic device 100 from aligning with any corneal astigmatism present in the wearer.

The enclosure 104 may additionally include one or more fenestrations 114. Each of the fenestrations 114, which may be holes or openings through the enclosure 104, may be located at a radius outside of the insert 102. The fenestrations 114 may extend from the anterior side of the enclosure 104 to intersect with a respective one of the channels 112 on the posterior side of the enclosure 104. The fenestrations 114 may be from 100 to 1000 microns in diameter, for example. In some embodiments, the fenestrations 114 may be 400 to 500 microns in diameter.

A combination of the channels 112 and the fenestrations 114 may provide a pathway or conduit for the exchange of tear fluid between the tear fluid chamber and an area external to the ophthalmic device 100. For example, tear fluid may propagate through one or more of the fenestrations 114 and their respective channels 112 to reach the tear fluid chamber, which may provide fresh tear fluid and oxygen to maintain ocular health. Conversely, old tear fluid may escape the tear fluid chamber through the channels 112 and fenestrations 114 while transporting mucus and debris away from the central cornea area.

The enclosure 104 may further include one or more offset features 116. Each of the offset features 116 may be formed radially internal of the diameter of the insert 102. The one or more offset features 116, which may be non-rotationally symmetric, may be formed in the enclosure 104 to provide clearance between the insert 102 and the enclosure 104. For example, the offset features 116 may provide around 100 microns of clearance between the insert 102 and the enclosure 104. In some embodiments, the one or more offset features 116 may be formed in or on the anterior portion of the enclosure 104, which may provide clearance between an anterior side of the insert 102 and an internal surface of the anterior portion of the enclosure 104. Alternatively or additionally, the one or more offset features 116 may be formed in the posterior portion of the enclosure 104, and provide clearance between an internal surface of the posterior portion of the enclosure 104 and the posterior side of the insert 102. The one or more offset features 116 may also be alignment features that provide alignment in a direction normal to the ophthalmic device 100, e.g., in the optical axis direction. In some embodiments, the one or more offset features 116 may be bumps formed in the enclosure 104.

Further, the enclosure 104 includes one or more alignment features 118. The one or more alignment features 118 may be formed radially outside of the diameter of the insert 102. The one or more alignment features 118 may be formed in the enclosure 104 to provide alignment fiducials to aid in assembly of the ophthalmic device 100. For example, the one or more alignment features 118 may provide radial alignment of the insert 102 to the enclosure 104 so to obtain centration of the insert 102. In some embodiments, the one or more alignment features 118 may be formed in or on the anterior portion of the enclosure 104. Alternatively or additionally, the one or more offset features 116 may be formed in the posterior portion of the enclosure 104. In some embodiments, the one or more offset features 116 may be bumps formed in the enclosure 104.

While FIG. 1 shows three offset and alignment features 116 and 118, respectively, the number of offset and alignment features is a non-limiting aspect of the present disclosure. In general, any number and/or arrangement of offset and alignment features that provide non-rotational symmetry me included in the ophthalmic device 100. Additionally, any shape other than bumps is contemplated by the present disclosure, and the bumps example should not be considered limiting.

The skirt 108 may be an area or portion of the enclosure 104 that conforms to a user's eye outside of the cornea. The skirt 108 may anchor the ophthalmic device 100 in position, while allowing for movement and removal of the ophthalmic device 100. For example, the skirt 108 may be flexible so that a user may be able to pinch it to remove the ophthalmic device 100 from their eye. Additionally, the skirt 108 may provide a gradual decrease in the thickness of the ophthalmic device 100 so to be more comfortable to the eye and to blinking of the eye. In some embodiments, the radius of curvature of the enclosure 104 in the skirt 108 area may be less than the radius of curvature of the enclosure 104 in the optic area 106.

Figure 2:
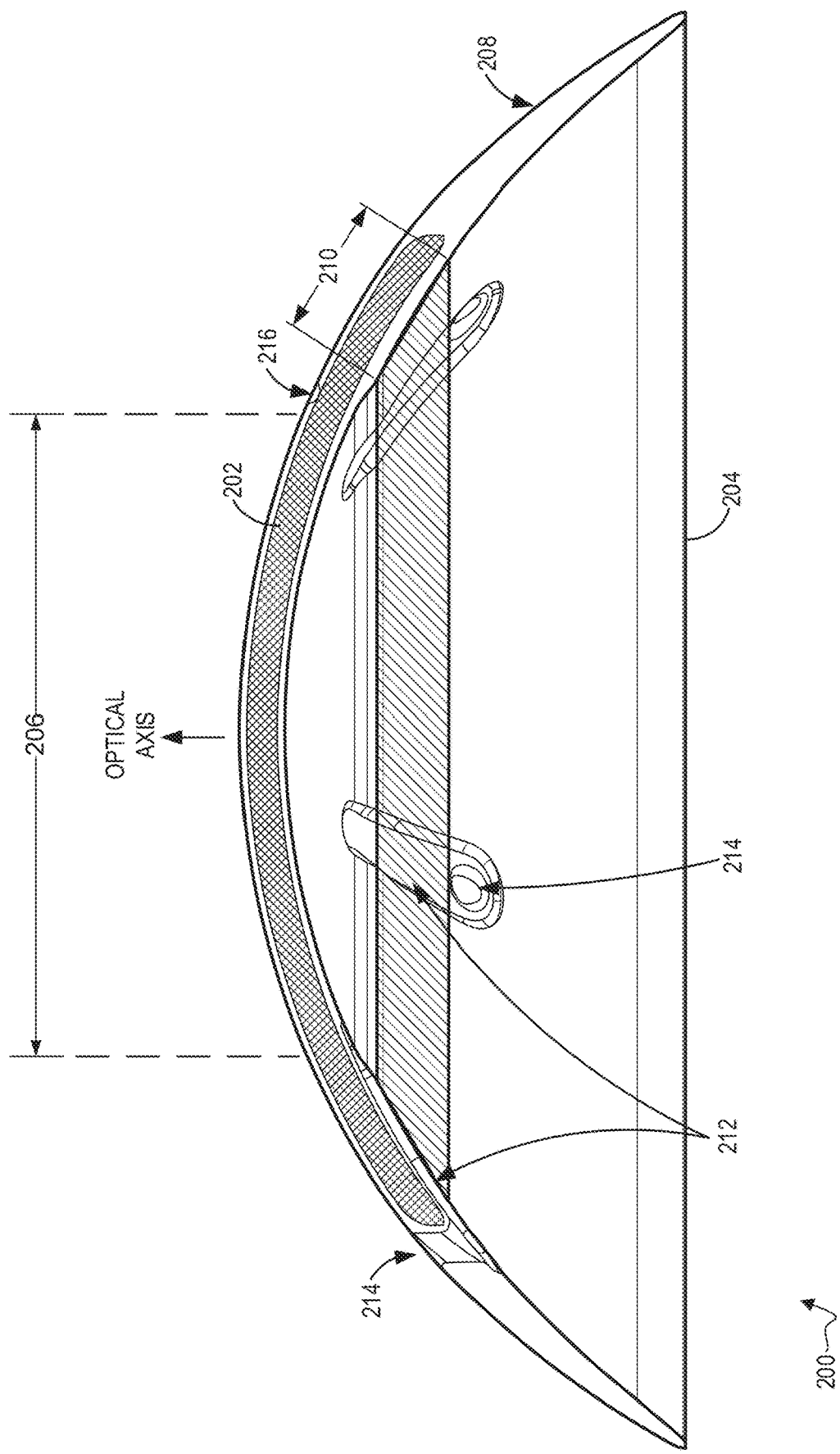
FIG. 2 is an illustrative perspective view of an ophthalmic device including posterior and anterior features in accordance with an embodiment of the disclosure.

FIG. 2 is an illustrative cross-sectional view of an ophthalmic device 200 including posterior and anterior features in accordance with the present disclosure. The ophthalmic device 200 may be an example of the ophthalmic device 100. The ophthalmic device 200 may be an on-eye wearable contact ophthalmic device, which may at least provide optical benefits to a wearer.

The illustrated embodiment of the ophthalmic device 200 includes an insert 202 disposed in an enclosure 204. The enclosure 204 may include a cornea contact 210, a plurality of channels 212, a plurality of fenestrations 214, and a plurality of offset features 216 (only one of which is shown). The various features may be similar to like features of the ophthalmic device 100. The ophthalmic device 200 may have a concave side (facing down in FIG. 2), and a convex side (facing up in FIG. 2). The concave side may also be referred to as the posterior side, whereas the convex side may also be referred to as the anterior side. The ophthalmic device 200 may be worn on a user's eye, for example, with the concave side fitting onto the eye.

The plurality of offset features 216 may be formed on the convex side of the ophthalmic device 200, and may provide clearance between the insert 202 and an internal surface of the enclosure 204. The plurality of offset features 216, which may be bumps formed in/on the anterior side of the enclosure 204, may be formed inside the diameter of the insert 202. Additionally, the plurality of offsets 216 may provide alignment features in the direction of the optical axis of the ophthalmic device 200. While not shown in FIG. 2, the ophthalmic device 200 may further, at least in some embodiments, include a plurality of alignment features formed in the enclosure 204 and formed radially outside of the insert 202, which may be similar to the one or more alignment features 118.

The cornea contact 210 may provide a broken, or discontinuous, ring of contact area intended to contact a perimeter of a user's cornea. While the lined area shown in FIG. 2 to show the location of the cornea contact 210 does not show breaks, the ring would be broken where each of the plurality of channels 212 occur, for example, and the cornea contact 210 may not contact the cornea in the breaks. The cornea contact 210 may be formed in or on the concave side of the enclosure 204 and formed under a perimeter area of the insert 202. The cornea contact 210 may provide a buffer area for resting the ophthalmic device 200 on a user's eye, and may further improve the comfort of the ophthalmic device 200. In some embodiments, the insert 202 may affect the comfort of the ophthalmic device 200, so the cornea contact 210 may be disposed under the perimeter of the insert 202 to affect the comfort of the ophthalmic device 200. The cornea contact 210 may be raised relative to the concave side of the ophthalmic device 200 inside the diameter of the cornea contact 210, e.g., the optic area 206. In some embodiments, the cornea contact 210 may not be raised outside of the perimeter of the insert 202, and may instead blend into the skit 208. This raised area may not contact the central cornea of the user's eye, which may provide clearance between the eye and the concave side of the optic area 206, at least within the cornea contact 210 ring. The height of the clearance may allow the ophthalmic device 200 to fit a wide variety of eye shapes, a majority of the eye population for example. This volume of space formed between the cornea and the ophthalmic device 200 may form a tear fluid chamber, for example, and may hold tear fluid.

The plurality of channels 212 may be formed in or on the enclosure 204 and may extend through the cornea contact 210. Each of the channels 212 may extend from a radius outside of the insert 202 radius to a radius internal of the insert 202 radius. For example, each of the channels 212 may extend from just outside of the insert 202 to an inner edge of the cornea contact 210. In some embodiments, however, one or more channels 212 of the plurality of channels 212 may extend through the skirt 208 to an edge of the enclosure 204.

The plurality of fenestrations 214 may extend through the enclosure 204 and intersect with a proximate end of a respective one of the plurality of channels 212. Each of the plurality of fenestrations 214 may extend from the convex side to the concave side of the ophthalmic device 200. On the concave side, the fenestrations 214 may couple to a respective one of the channels 212 so that an unobstructed path, e.g., a conduit, may be formed through the enclosure 204. The plurality of fenestrations 214 may be formed outside of the insert 202.

The combination of the plurality of channels 212 and the plurality of fenestrations 214 may form pathways/conduits between the tear fluid chamber and the eye external to the ophthalmic device 200. The pathways may allow for the exchange of tear fluid between the tear fluid chamber and the eye external to the ophthalmic device 200 so to refresh the tear fluid in the tear fluid chamber to maintain ocular health while wearing the ophthalmic device 200.

In some embodiments, the concave side of the enclosure 204 may have a different radius of curvature in the optic area 206 than in the skirt area 208. Further, the concave side of the insert 202 may have a radius of curvature that is different than the corresponding radius of curvature of the enclosure 204. The various radii of curvature, however, may desirably be formed so that the ophthalmic device 200 may fit a majority of the eye population. The clearance between the central cornea and the concave side of the ophthalmic device 200 due to the height of the cornea contact 210 may also affect the fit of the ophthalmic device 200.

Figure 3:
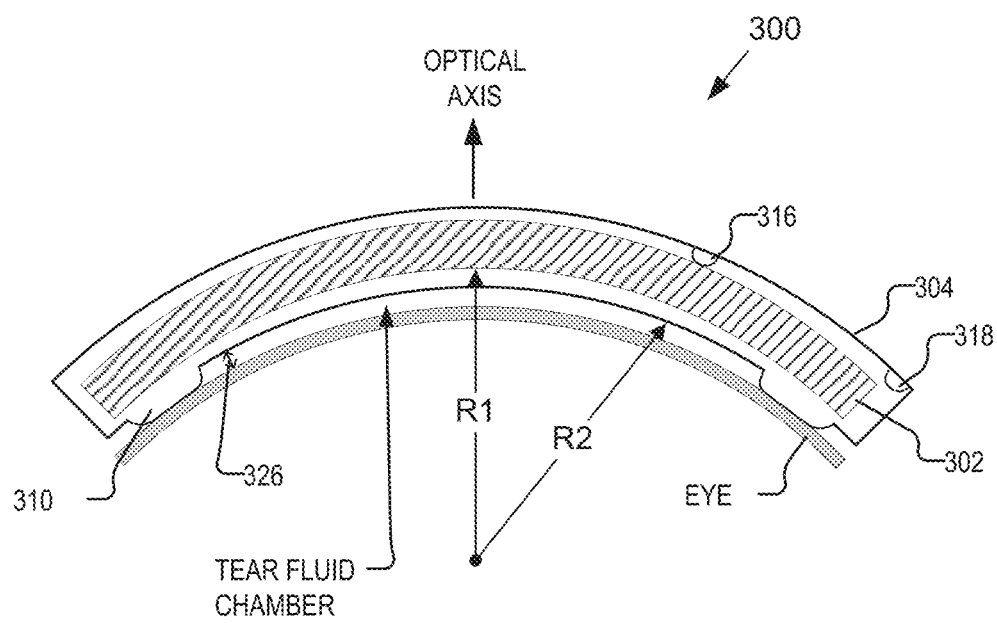
FIG. 3 is an illustrative cross-sectional view of a central area of an ophthalmic device including posterior and anterior features in accordance with an embodiment of the disclosure.

FIG. 3 is an illustrative cross-sectional view of a central area of an ophthalmic device 300 including posterior and anterior features in accordance with an embodiment of the present disclosure. The ophthalmic device 300 may be an example of the ophthalmic device 100. The illustrated embodiment of the ophthalmic device 300 includes an insert 302 and an enclosure 304. While the ophthalmic device 300 is not shown to include a skirt area, comparable to the skirt 108, the skirt area is omitted to focus on various features in the central area of the ophthalmic device 300.

A posterior side of the insert 302 may have a radius of curvature R1. R1 may desirably be selected, based on a statistical analysis of a large population of eye shapes and sizes, to fit a majority of the eye population. Further, a posterior side of the enclosure 304 may have a radius of curvature R2. As with the insert, R2 may desirably be selected, based on a statistical analysis of a large population of eye shapes and sizes, to fit a majority of the eye population. In some embodiments, R1 and R2 may allow the ophthalmic device 300 to fit greater than 95% of the eye population, for example. In some embodiments, R1 and R2 may be different. For example, R1 may be around 8.5 mm whereas R2 may be around 8 mm.

The enclosure 304 may include an offset feature 316 and an alignment feature 318. The offset and alignment features 316 and 318, respectively, may be bumps formed in or on an anterior side of the enclosure 304. The offset features 316 may be formed inside of a diameter of the insert 302, and may assist in alignment of the insert 302 and the enclosure 304 in a direction parallel to the optical axis of the ophthalmic device 300. Further, the offset features 316 may form clearance between an anterior side of the insert 302 and an internal surface of the anterior side of the enclosure 304. In some embodiments, the clearance may be around 100 microns, but other clearance amounts are within the scope of the present disclosure.

The alignment features 318 may be bumps formed in the posterior side of the enclosure 304, and may be formed outside a diameter of the insert 302. The alignment features 318 may provide alignment fiducials to aid assembly of the ophthalmic device 300. In some embodiments, the alignment features 318 may cause centration of the insert 302 within the enclosure 304.

The enclosure 304 may also include cornea contact 310. Cornea contact 310 may be formed in/on the posterior side of the enclosure 304, and may provide a cornea contact area. The cornea contact area may aid in comfort of the ophthalmic device 300 while being worn by a user. In some embodiments, the cornea contact 310 may be shaped into a discontinuous contoured profile, and arranged between a perimeter of the insert 302 and the surface of the eye. The height 326 of the cornea contact, at least with respect to a posterior side of the enclosure 304 within the cornea contact 310, may provide clearance of the posterior side of the enclosure 304 within the cornea contact 310 and the eye. This clearance, which may range from 50 to 200 microns, may further allow the ophthalmic device to be worn by a majority of the eye population. The cornea contact 310 may further has a radius of curvature that may be in the range of a natural radius of curvature of a user's eye surface, e.g., it may mimic the cornea curvature in the area of contact, and may not be a feature on the posterior side of the enclosure 304 that excessively deforms the cornea, for example. Accordingly, the clearance created by the cornea contact 310 and the radius of curvature of the cornea contact 310 may add to the comfort of the ophthalmic device 300.

The clearance between the eye and the posterior side of the enclosure 304 within the cornea contact 310 may further form a tear fluid chamber. The tear fluid chamber may be defined by the surface of the eye, the posterior side of the enclosure 304 and the cornea contact 310. The tear fluid chamber may provide a volume for tear fluid to accumulate, which may provide for ocular health. While not shown in the ophthalmic device 300, channels and fenestrations, similar to the channels 112 and fenestrations 114, may be included in the enclosure 304. The channels and fenestrations may provide a conduit for the exchange of tear fluid and oxygen between the tear fluid chamber and the eye external to the ophthalmic device 300. The exchange of tear fluid may allow fresh tear fluid and oxygen to reach the central cornea area, while transporting mucus and debris away from the central cornea area.

While the cornea contact 310 is shown as a raised area of the enclosure 304, in some embodiments only the side adjacent to the tear fluid chamber may be raised from the eye. In such an embodiment, the cornea contact 310 may blend into the enclosure 304 radially outward and continue to contact the eye in a direction toward the sclera.

Figure 4:
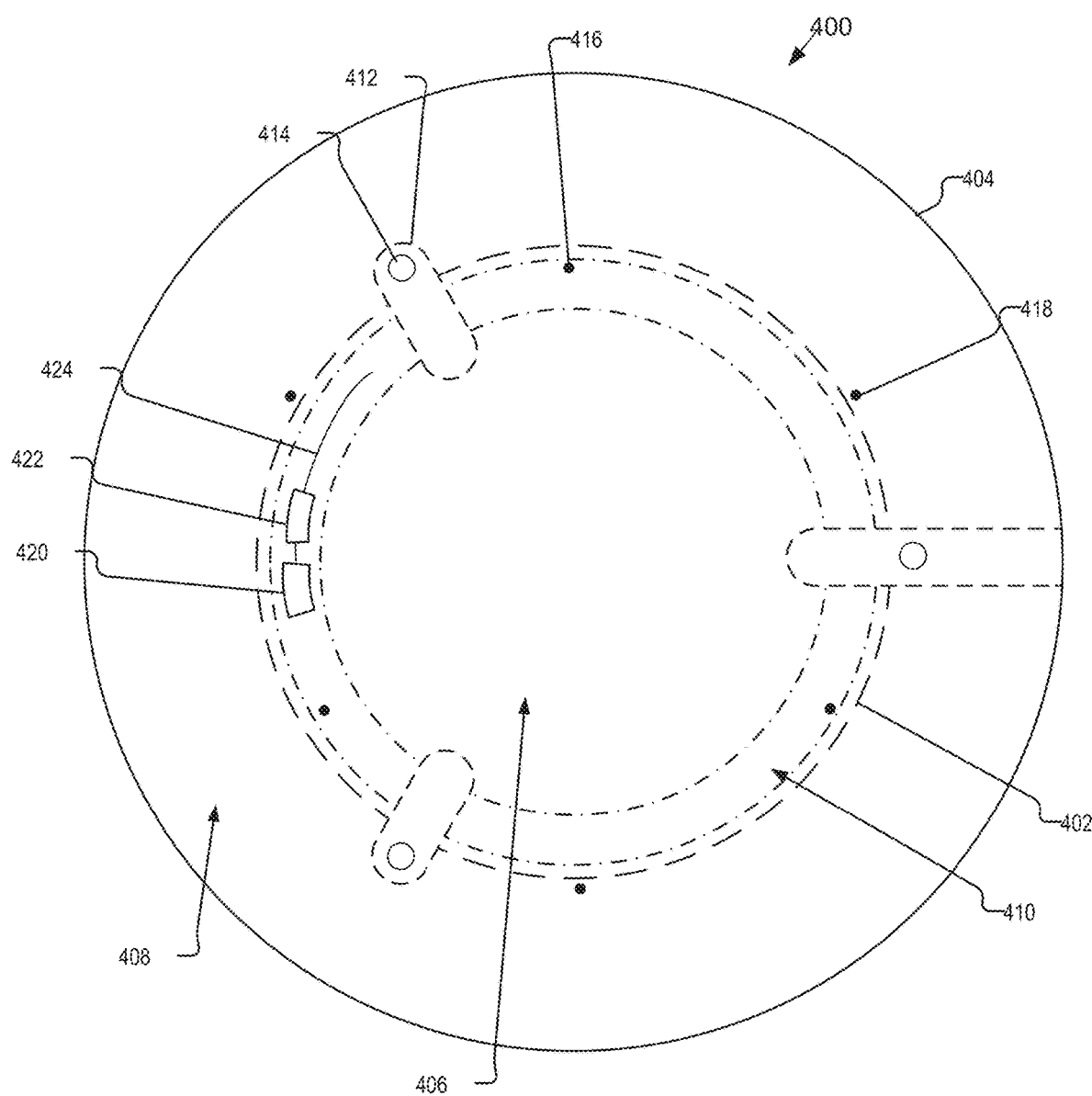
FIG. 4 is an illustrative plan view of an ophthalmic device including posterior and anterior features in accordance with an embodiment of the disclosure.

FIG. 4 is an illustrative plan view of an ophthalmic device 400 including posterior and anterior features in accordance with an embodiment of the present disclosure. The ophthalmic device 400, which may be similar to the ophthalmic device 100 in may aspects, may include various electronics to control a dynamic optic, for example. The illustrated embodiment of the ophthalmic device 400 includes an insert 402, an enclosure 404, control electronics 420 and 422, and an antenna 424. The ophthalmic device 400 may be an on-eye wearable device or an intraocular device, and may provide accommodation to a user, for example.

The insert 402 may be formed from soft or rigid biocompatible materials, and may be disposed within the enclosure 404. The insert 402 may at least provide dynamic optical power to a user. For example, the insert 402 may include a dynamic optic based on liquid crystal or electrowetting techniques. The dynamic optic of the insert 402, which may be arranged in the optic area 406, may be controlled by the control electronics 420 and/or 422, which may be included in or on a layer of the insert 402. In some embodiments, the insert 402 may additionally include static optical power. The insert 402 may further be formed from a plurality of optical elements arranged into a stack, which may include a substrate for the control electronics 420, 422, and the antenna 424.

The control electronics 420 and 422 may include various logic, circuits, power supplies, and batteries for controlling the dynamic optic and for communication with components external to the ophthalmic device 400. The antenna 424, which may include multiple separate antennae in some embodiments, may be used to send and receive communication signals and/or for wireless charging of related batteries and or power supplies.

The disclosed embodiment of the enclosure 404 includes a cornea contact 410, channels 412, fenestrations 414, offset features 416, and alignment features 418. These various features and geometries, which may be similar to like features and geometries of ophthalmic devices 100, 200 and 300, may not be discussed in detail for sake of brevity. The offset features 416, which may be bumps formed in/on an anterior side of the enclosure 404, may form a clearance between the insert 402 and an internal surface of the enclosure 404. Further, the offset features 416 may provide alignment in a direction normal to the optic area 406. The alignment features 418, which may be bumps formed in the anterior side of the enclosure 404, may provide alignment fiducials to aid in centering the insert 402 within the enclosure 404.

The cornea contact 410 may be a discontinuous ring formed in or on a posterior side of the enclosure, and disposed under a perimeter of the insert 402. The cornea contact 410 may provide vault to the optic area 406, which may form a clearance over a user's central cornea area. This clearance may form a volume of space, such as the tear fluid chamber discussed above.

The channels and fenestrations 412 and 414, respectively, may be formed in the enclosure 404. For example, the channels 412 may be formed on the posterior side of the enclosure 404 and may extend through the cornea contact 410, which may form the discontinuous portions of the cornea contact 410. The channels 412 may extend from a radius outside of the insert 402 to at least an inner radial edge of the cornea contact 410. Additionally, the channels 412 may intersect with, e.g., couple to, respective ones of the fenestrations 414 radially outside of the insert 402. The channels and fenestrations 412 and 414, respectively, may combine to form a conduit for the exchange of tear fluid between the tear fluid chamber and the eye external to the ophthalmic device 400. In some embodiments, one or more of the channels 412 may extend to an outer edge of the enclosure 404, which may or may not intersect with a fenestration 414.

The skirt 408 may provide a soft area outside of the insert 402 that may promote ease of removal of the ophthalmic device 400. For example, the skirt 408 may be pinched by a user when removing the ophthalmic device 400. Additionally, the channels and fenestrations 412 and 414, respectively, may assist with removal by preventing the occurrence of suction of the ophthalmic device 400 onto the user's eye.

Figure 5:
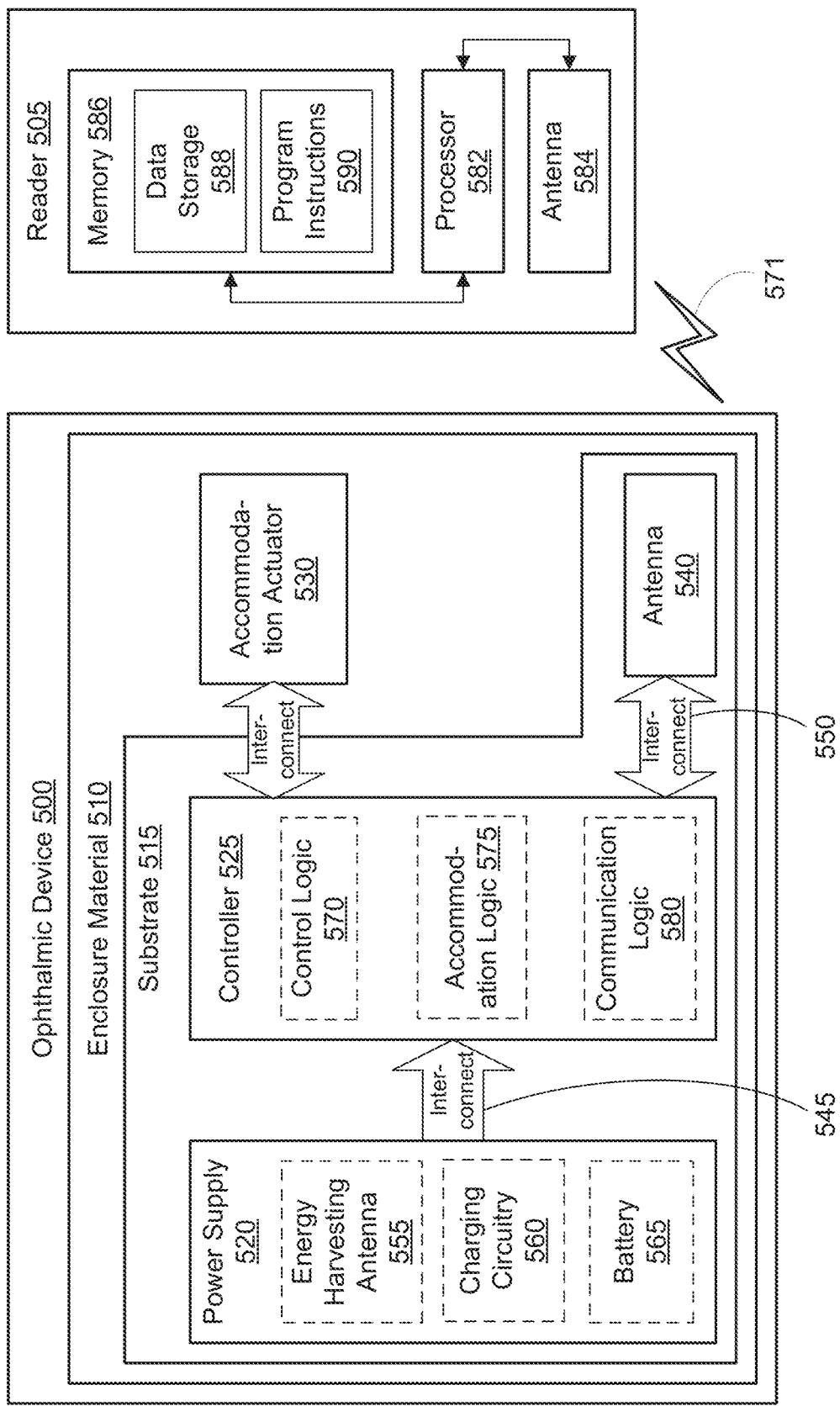
FIG. 5 is a functional block diagram of an ophthalmic device including posterior and anterior features in accordance with an embodiment of the disclosure.

FIG. 5 is a functional block diagram of an ophthalmic device 500 including posterior and anterior features in accordance with an embodiment of the present disclosure. Ophthalmic device 500 may be an on-eye device, such as a contact lens or a smart contact lens, or an implantable device, such as an intraocular lens. In the depicted embodiment, ophthalmic device 500 includes an enclosure material 510 formed to be either contact-mounted to a corneal surface of an eye or implanted into an eye. The enclosure material 510 may be one implementation of the enclosure 104. A substrate 515 is embedded within or surrounded by enclosure material 510 to provide a mounting surface for a power supply 520, a controller 525, an antenna 540, and various interconnects 545 and 550. The substrate 515 and the associated electronics may be one implementation of the control electronics 420 and/or 422. Additionally, the substrate 515 may be included with the insert 402, such as on a perimeter area of the insert 402. The illustrated embodiment of power supply 520 includes an energy harvesting antenna 555, charging circuitry 560, and a battery 565. The illustrated embodiment of controller 525 includes control logic 570, accommodation logic 575, and communication logic 580. As shown, accommodation actuator 530 is disposed in the enclosure material 510.

Power supply 520 supplies operating voltages to the controller 525 and/or the accommodation actuator 530. Antenna 540 is operated by the controller 525 to communicate information to and/or from ophthalmic device 500. In the illustrated embodiment, antenna 540, controller 525, and power supply 520 are disposed on/in substrate 515, while accommodation actuator 530 is disposed in enclosure material 510 (not in/on substrate 515). However, in other embodiments, the various pieces of circuitry and devices contained in ophthalmic device 500 may be disposed in/on substrate 515 or in enclosure material 510, depending on the specific design of ophthalmic device 500. For example, in one embodiment, accommodation actuator 530 may be disposed on a transparent substrate.

Substrate 515 includes one or more surfaces suitable for mounting controller 525, power supply 520, and antenna 540. Substrate 515 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 515 to form circuitry, electrodes, etc. For example, antenna 540 can be formed by depositing a pattern of gold or another conductive material on substrate 515. Similarly, interconnects 545 and 550 can be formed by depositing suitable patterns of conductive materials on substrate 515. A combination of resists, masks, and deposition techniques can be employed to pattern materials on substrate 515. Substrate 515 can be a relatively rigid material, such as polyethylene terephthalate ("PET"), parylene or another material sufficient to structurally support the circuitry and/or electronics within enclosure material 510. Ophthalmic device 500 can alternatively be arranged with a group of unconnected substrates rather than a single substrate 515. For example, controller 525 and power supply 520 can be mounted to one substrate 515, while antenna 540 is mounted to another substrate 515 and the two can be electrically connected via interconnects. Substrate 515 may also be a continuous piece of semiconductor, housing all or some of the aforementioned pieces of device architecture as integrated circuitry.

Substrate 515 can be shaped as a flattened ring with a radial width dimension sufficient to provide a mounting platform for the embedded electronic components. Substrate 515 can have a thickness sufficiently small to allow substrate 515 to be embedded in enclosure material 510 without adversely influencing the profile of ophthalmic device 500. Substrate 515 can have a thickness sufficiently large to provide structural stability suitable for supporting the electronics mounted thereon. For example, substrate 515 can be shaped as a ring with a diameter of about 10 millimeters, a radial width of about 1 millimeter (e.g., an outer radius 1 millimeter larger than an inner radius), and a thickness of about 50 micrometers. Substrate 515 can optionally be aligned with the curvature of the eye-mounting surface of ophthalmic device 500 (e.g., convex surface). For example, substrate 515 can be shaped along the surface of an imaginary cone between two circular segments that define an inner radius and an outer radius. In such an example, the surface of substrate 515 along the surface of the imaginary cone defines an inclined surface that is approximately aligned with the curvature of the eye mounting surface at that radius.

In the illustrated embodiment, power supply 520 includes a battery 565 to power the various embedded electronics, including controller 525. Battery 565 may be inductively charged by charging circuitry 560 and energy harvesting antenna 555. In one embodiment, antenna 540 and energy harvesting antenna 555 are independent antennae, which serve their respective functions of energy harvesting and communications. In another embodiment, energy harvesting antenna 555 and antenna 540 are the same physical antenna that are time shared for their respective functions of inductive charging and wireless communications with reader 505. Additionally or alternatively, power supply 520 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 560 may include a rectifier/regulator to condition the captured energy for charging battery 565 or directly power controller 525 without battery 565. Charging circuitry 560 may also include one or more energy storage devices to mitigate high frequency variations in energy harvesting antenna 555. For example, one or more energy storage devices (e.g., a capacitor, an inductor, etc.) can be connected to function as a low-pass filter.

Controller 525 contains logic to choreograph the operation of the other embedded components. Control logic 570 controls the general operation of ophthalmic device 500, including providing a logical user interface, power control functionality, etc. Accommodation logic 575 includes logic for receiving signals from sensors monitoring the orientation of the eye, determining the current gaze direction, focal distance of the user and/or relative position of the eyelid, and manipulating accommodation actuator 530 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 580 provides communication protocols for wireless communication with reader 505 via antenna 540. In one embodiment, communication logic 580 provides backscatter communication via antenna 540 when in the presence of an electromagnetic field 571 output from reader 505. In one embodiment, communication logic 580 operates as a smart wireless radio-frequency identification ("RFID") tag that modulates the impedance of antenna 540 for backscatter wireless communications. The various logic modules of controller 525 may be implemented in software/firmware executed on a general purpose microprocessor, in hardware (e.g., application specific integrated circuit), or a combination of both.

Ophthalmic device 500 may include various other embedded electronics and logic modules. For example, a light source or pixel array may be included to provide visible feedback to the user. An accelerometer or gyroscope may be included to provide positional, rotational, directional or acceleration feedback information to controller 525.

The illustrated embodiment also includes reader 505 with a processor 582, an antenna 584, and memory 586. Memory 586 in reader 505 includes data storage 588 and program instructions 590. As shown reader 505 may be disposed outside of ophthalmic device 500, but may be placed in its proximity to charge ophthalmic device 500, send instructions to ophthalmic device 500, and/or extract data from ophthalmic device 500. In one embodiment, reader 505 may resemble a conventional contact lens holder that the user places ophthalmic device 500 in at night to charge, extract data, clean the lens, etc.

External reader 505 includes an antenna 584 (or group of more than one antennae) to send and receive wireless signals 571 to and from ophthalmic device 500. External reader 505 also includes a computing system with a processor 582 in communication with a memory 586. Memory 586 is a non-transitory computer-readable medium that can include, without limitation, magnetic disks, optical disks, organic memory, and/or any other volatile (e.g., RAM) or non-volatile (e.g., ROM) storage system readable by the processor 182. Memory 586 can include a data storage 588 to store indications of data, such as data logs (e.g., user logs), program settings (e.g., to adjust behavior of ophthalmic device 500 and/or external reader 505), etc. Memory 586 can also include program instructions 590 for execution by processor 582 to cause the external reader 505 to perform processes specified by the instructions 590. For example, program instructions 590 can cause external reader 505 to provide a user interface that allows for retrieving information communicated from ophthalmic device 500 or allows transmitting information to ophthalmic device 500 to program or otherwise select operational modes of ophthalmic device 500. External reader 105 can also include one or more hardware components for operating antenna 584 to send and receive wireless signals 571 to and from ophthalmic device 500.

External reader 505 can be a smart phone, digital assistant, or other portable computing device with wireless connectivity sufficient to provide the wireless communication link 571. External reader 505 can also be implemented as an antenna module that can be plugged into a portable computing device, such as in an embodiment where the communication link 571 operates at carrier frequencies not commonly employed in portable computing devices. In some instances, external reader 505 is a special-purpose device configured to be worn relatively near a wearer's eye to allow the wireless communication link 571 to operate with a low power budget. For example, the external reader 505 can be integrated in a piece of jewelry such as a necklace, earring, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
an enclosure having an insert disposed therein, the enclosure including:
a cornea contact disposed on a posterior side of the enclosure and arranged to rest on a user's cornea outside of a central cornea area when the ophthalmic device is worn by a user; and
a channel formed in the posterior side of the enclosure, wherein the channel extends through the cornea contact from at least radially outside of the insert to an inner edge of the cornea contact; and
a plurality of offset features formed in the enclosure and radially inside of the insert, each of the plurality of offset features configured to provide clearance between the insert and a surface of the enclosure.

2. The ophthalmic device of claim 1, further comprising:
a plurality of alignment features formed in the enclosure and disposed radially outside of the insert, the plurality of alignment features configured to provide alignment markers for aligning an optical axis of the insert with a central axis of the enclosure.

3. The ophthalmic device of claim 2, wherein the plurality of offset features and the plurality of alignment features are formed in an anterior side of the ophthalmic device or a posterior side of the ophthalmic device.

4. The ophthalmic device of claim 1, further comprising:
a fenestration formed through the enclosure, wherein the fenestration is disposed radially outside of the insert and positioned to intersect with the channel radially outside of the insert and radially outside of the cornea contact.

5. The ophthalmic device of claim 4, wherein the enclosure includes a plurality of channels and a plurality of fenestrations, and wherein each of the plurality of fenestrations intersect with an end of a respective one of the plurality of channels.

6. The ophthalmic device of claim 5, wherein at least one of the plurality of channels extend all the way to a perimeter edge of the enclosure.

7. The ophthalmic device of claim 5, wherein the plurality of fenestrations and the plurality of channels provide a conduit for tear fluid exchange between a tear fluid chamber and the eye external to the ophthalmic device.

8. The ophthalmic device of claim 7, wherein the tear fluid chamber is a volume of space between a user's eye and a posterior side of the enclosure and encircled by the cornea contact.

9. The ophthalmic device of claim 1, wherein the cornea contact comprises a toroidal-shaped ring that raises from the posterior side of the enclosure.

10. The ophthalmic device of claim 9, wherein the toroidal-shaped ring has at least one discontinuous section through which the channel extends and wherein the toroidal-shaped ring extends at least partially under the insert.

11. The ophthalmic device of claim 1, wherein the insert is a rigid, gas permeable polymeric insert that provides optical power and the enclosure is formed from a hydrogel or a silicone hydrogel.

12. An ophthalmic device, comprising:
a rigid insert; and
an enclosure enveloping the rigid insert, wherein the enclosure includes:
a cornea contact formed on a concave side of the enclosure, the cornea contact having a toroidal-shape that protrudes from the concave side of the enclosure and is disposed under at least a portion of the rigid insert, wherein the toroidal-shape of the cornea contact includes a plurality of discontinuous sections; and
a plurality of channels formed on the concave side of the enclosure and each extending through a corresponding one of the discontinuous sections of the cornea contact.

13. The ophthalmic device of claim 12, further comprising:
a plurality of offset features formed in the enclosure and inside a diameter of the rigid insert, each of the plurality of offset features configured to provide clearance between an anterior side of the rigid insert and a surface of the enclosure.

14. The ophthalmic device of claim 12, further comprising:
   a plurality of alignment features formed in the enclosure and outside a diameter of the rigid insert, the plurality of alignment features configured to provide alignment markers for aligning an optical axis of the rigid insert with a central axis of the enclosure.

15. The ophthalmic device of claim 14, wherein each of the plurality of alignment features is formed in an anterior side of the enclosure.

16. The ophthalmic device of claim 12, wherein a radius of curvature of a concave side of the rigid insert is different than a radius of curvature of the concave side of the enclosure.

17. The ophthalmic device of claim 12, further comprising:
   a plurality of fenestrations formed through the enclosure and radially outside of the rigid insert, each of the plurality of fenestrations intersecting with a respective one of the plurality of channels.

18. The ophthalmic device of claim 17, wherein the cornea contact raises an optic area of the ophthalmic device so that there is clearance between a surface of a user's cornea and the concave side of the enclosure within the cornea contact, and wherein a space between the user's cornea and the concave side of the enclosure within the cornea contact forms a tear fluid chamber, and wherein the plurality of channels and the plurality of fenestrations allow exchange of tear fluid between the tear fluid chamber and the user's eye.

19. The ophthalmic device of claim 12, wherein at least one of the plurality of channels extends to a perimeter edge of the enclosure.

20. An ophthalmic device, comprising:
   an enclosure having an insert disposed therein, the enclosure including:
      a cornea contact disposed on a posterior side of the enclosure and arranged to rest on a user's cornea outside of a central cornea area when the ophthalmic device is worn by a user; and
      a channel formed in the posterior side of the enclosure, wherein the channel extends through the cornea contact from at least radially outside of the insert to an inner edge of the cornea contact; and
   a plurality of alignment features formed in the enclosure and disposed radially outside of the insert, the plurality of alignment features configured to provide alignment markers for aligning an optical axis of the insert with a central axis of the enclosure.

* * * * *